United States Patent [19]

Hanaoka et al.

[11] Patent Number: 5,747,502
[45] Date of Patent: May 5, 1998

[54] PROCESS FOR PREPARING BENZO[C] PHENANTHRIDINIUM DERIVATIVES, NOVEL COMPOUNDS PREPARED BY SAID PROCESS, AND ANTITUMOR AGENTS

[75] Inventors: Miyoji Hanaoka, Kanazawa; Hisao Ekimoto; Fumiko Kobayashi, both of Tokyo; Yukio Irie, Maebashi; Katsutoshi Takahashi, Tokyo; Masanobu Suzuki, Omiya; Takeshi Nakanishi, Yono; Osamu Kogawa, Kashiwa; Keizou Ishikawa, Iwatsuki, all of Japan

[73] Assignee: Nippon Kayaku Kabushiki Kaisha, Tokyo, Japan

[21] Appl. No.: 851,853

[22] Filed: Mar. 16, 1992

Related U.S. Application Data

[63] Continuation-in-part of Ser. No. 784,699, Oct. 30, 1991, abandoned, and Ser. No. 621,848, Dec. 4, 1990, abandoned.

[30] Foreign Application Priority Data

| Dec. 13, 1989 | [JP] | Japan | 1-321503 |
| Nov. 7, 1990 | [JP] | Japan | 2-299844 |
| Jun. 11, 1991 | [JP] | Japan | 3-165174 |
| Jun. 11, 1991 | [JP] | Japan | 3-165175 |

[51] Int. Cl.$^6$ .................... A61K 31/44; C07D 471/00
[52] U.S. Cl. .................... 514/280; 514/883; 514/908; 546/42
[58] Field of Search .................. 546/42, 61; 514/280, 514/284

[56] References Cited

U.S. PATENT DOCUMENTS

| 3,912,740 | 10/1975 | Zee-Cheng et al. | 260/286 |
| 4,014,885 | 3/1977 | Zee-Cheng et al. | 260/289 |
| 4,767,626 | 8/1988 | Cheng | 424/195.1 |

OTHER PUBLICATIONS

Hanaoka, Tetrahedron Letters, vol. 25, No. 45, pp. 5169–5172, (1984) Transformation of Protoberberines Into Benzo[c]phenanthridine a Novel and Efficient Synthesis of Antitumor Benzo[c]phenanthridine Alkaloids, Fagaronine and Nitidine.

Chemical Pharmaceutical Bulletin, vol. 33, No. 4, pp. 1763–1765, (1985) Miyoji Hanaoka et al. Synthesis of Fagaridine, A Phenolic Benzo[c]phenanthridine Akaloid.

Chemical Pharmaceutical Bulletin, vol. 33, No. 10, pp. 4139–4151, (1985) Hisashi Ishii, et al. Studies on the Chemical Constituents of Rutaceous Plants. LX. Development of a Versatile Method For Syntheses of the Antitumor Benzo[c]phenanthridine Alkaloids. (9). Efficient Synthesis and Antitumor Activities of Nitidine and Related Nonphenolic Benzo[c]phenanthridine Alkaloids.

Larock, Richard C. Comprehensive Organic Transformations, pp. 89–90 (1990).

Kakiuchi Planta medica, 1987, pp. 22–27, Effect of Benzo[c]phenanthridine Alkaloids on Reverse Transcriptase and Their Binding Property To Nucleic Acids.

Kessar, J.Org.Chem., vol. 53, 1708–1713 (1988). Benzyne Cyclization Route To Benzo[c]phenanthridine Alkaloids. Synthesis of Cherlerythrine, Decarine, and Nitidine.

Rosa, Tetrahedron Letters 31, 1881–1884 (1990). Aryl–Aryl Coupling Induced By n–Tributylstannyl Hydride An Efficient Phenanthridine Synthesis.

Chemical Abstracts, 107, (21) 1987, p. 799 198705c.

Journal of Pharmaceutical Sciences, 61 (11) 1972, pp. 1858–1859, Fagaronine, A New Tumor Inhibitor Isolated From Fagara Zanthoxyloides Lam. (Rutaceae).

Fitoterapia, 58 (2) 1987, pp. 123–126, S.K. Adesina Further New Constituents of Zanthoxylum Lepreieurii.

Primary Examiner—Richard D. Lovering
Attorney, Agent, or Firm—Nields, Lemack & Dingman

[57] ABSTRACT

The present invention relates to benzo[c]phenanthridinium derivative of the general formula A:

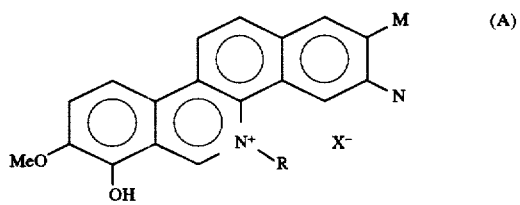

wherein M and N individually represent a hydroxyl or lower alkoxy group, or M and N simultaneously represent a hydrogen atom or together form a methylenedioxy group, X$^-$ represents an acid residue or a hydrogen acid residue, and R represents a lower alkyl group, and a process for preparing such derivatives. The compounds exhibit both potent antitumor activity and platelet aggregation inhibition activity, and are expected to be useful for the treatment of tumors. The process has good reproducibility and may be effected under moderate conditions, and therefore the process is practically useful. In addition, hydrogen salts of the present compounds have an enhanced stability, which is an advantage in formulating the same into pharmaceutical preparations.

12 Claims, No Drawings

PROCESS FOR PREPARING BENZO[C] PHENANTHRIDINIUM DERIVATIVES, NOVEL COMPOUNDS PREPARED BY SAID PROCESS, AND ANTITUMOR AGENTS

This application is a continuation-in-part of U.S. patent application Ser. No. 784,699 filed Oct. 30, 1991, now abandoned, and a continuation-in-part of U.S. patent application Ser. No. 621,848 filed Dec. 4, 1990, now abandoned.

BACKGROUND OF THE INVENTION

1. Field of the Invention

The present invention relates to compounds for medical use, pharmaceutical compositions useful for the prevention and treatment of malignant tumor in warm-blooded animals, and a novel process for preparing such compounds, which have antitumor activities and blood platelet aggregation inhibition activities and therefore may be expected as useful medicines. The invention also relates to antitumor agents containing said derivatives as effective ingredients.

2. Statement of the Prior Art

Nowadays, alkylating agents, nucleic acid metabolism antagonists antibiotics, plant alkaloids and the like have been used as chemotherapeutic drugs for patients with cancers.

It is also known that malignant tumors such as gastric cancer, lung cancer, etc. or diseases associated with hematopoietic organ, e.g., leukemia, etc. cause disseminated intravascular coagulation syndrome due to cancer or hypoxia, etc. which result in stimulation of endogenous and exogenous blood coagulation system [SOGO RINSHO (general clinic), 34, 2360–2364, 1985]. Accordingly, conventional chemotherapeutic agents are not effectively taken up into cancer cells to exhibit their activity.

It is also known that a thrombosis is caused by the cohesion and the coagulation of blood platelets, and has a relation with cerebral infarcts, cardiac disorders, cancerous DIC, etc., and also with a metastasis of cancers.

2,3-(methylenedioxy)-5-methyl-7-hydroxy-8-methoxybenzo[c]phenanthridinium chloride or iodide is a known compound described in Chem. Pharm. Bull., 33, 1763 (1985). It is also known from the disclosures of Japanese Patent Application KOKAI Nos. 2-243628 and 3-184916 that this compound has blood platelet aggregation inhibition activities and antitumor activities. Furthermore, Chem. Pharm. Bull., 33, 1763 (1985) describes a method for preparing the compound, wherein use is made of berberine as the starting material, which is treated in more than ten steps to obtain the aimed compound.

Furthermore, 5-methyl-7-hydroxy-8-methoxybenzo[c] phenanthridinium chloride or hydroxide having the general formula A, wherein M and N each are a hydrogen atom and X⁻ is Cl⁻ or OH⁻, is a known compound described in J. Org. Chem., 53, 1708–1713 (1988).

Accordingly, it has been desired to provide a simple and practically useful method for preparing benzo[c] phenanthridinium derivatives of the general formula A, and to develop antitumor agents which act on the blood coagulation system to show a preventative effect of blood coagulation and at the same time, an antitumor activity.

SUMMARY OF THE INVENTION

The compounds for medical application or pharmaceutical compositions of the present invention are useful for the treatment of malignant tumor of warm-blooded animals including human and exhibit an excellent antitumor activity not only against blood tumors but also against solid tumors.

The present inventors have made many studies on the production of benzo[c]phenanthridinium derivatives having the general formula A:

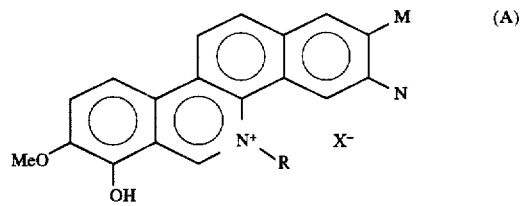

wherein M and N individually represent a hydroxyl or lower alkoxy group, or M and N simultaneously represent a hydrogen atom or together form a methylenedioxy group; X⁻ represents an acid residue or a hydrogen acid residue; and R represents a lower alkyl group.

As a result of these studies, a novel manufacturing method has been now found, which has a small number of steps, and which can practically be carried out even on a large scale to produce the aimed compounds in good yield, wherein use is made of a starting material which is different from that employed in the known method mentioned above.

In addition, it has been found that certain novel benzo[c] phenanthridinium derivatives, prepared by the present manufacturing process, have antitumor activities and blood platelet aggregation inhibition activities. The stability of the compounds according to the invention can be increased by converting them into their hydrogen salts, so that such hydrogen salts of the compounds have a merit in preparing pharmaceutical formulation thereof.

Also as a result of extensive studies, the present inventors have found that benzo[c]phenanthridinium derivatives shown by formula A have both the preventive effect of platelet aggregation and the antitumor activity and have thus achieved the present invention.

DETAILED DESCRIPTION OF THE INVENTION

Where the compound of formula A is used as a drug, the compound may usually be prepared into a pharmaceutical composition comprising the compound of formula A and pharmaceutical additives, and the composition is provided for use. An effective dose of the compound of formula A is administered to warm-blooded animal having a tumor, whereby growth of tumor can be inhibited, and tumor can be treated.

It is considered that when administered, the compound of the present invention would be dissociated in vivo as shown by the following formula A' where R, M and N are as defined above:

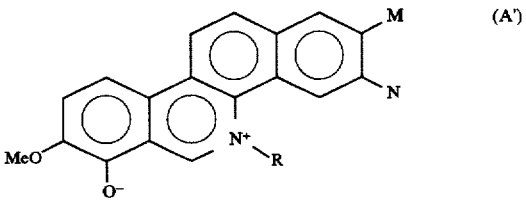

The invention also relates to a process for preparing a benzo[c]phenanthridinium derivative having the general formula A:

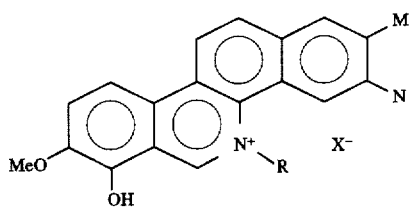

wherein M and N individually represent a hydroxyl or lower alkoxy group, or M and N simultaneously represent a hydrogen atom or together form a methylenedioxy group; X⁻ represents an acid residue or a hydrogen acid residue; and R represents a lower alkyl group, characterized in that a compound of the general formula C:

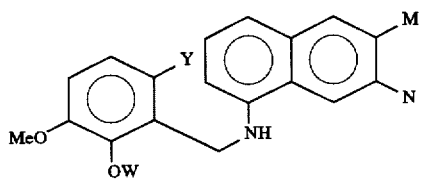

wherein M and N individually represent a hydroxyl or lower alkoxy group, or M and N simultaneously represent a hydrogen atom or together form a methylenedioxy group; Y represents a halogen atom; and W represents a protective group, is subjected to a ring closure reaction in the presence of an organic tin compound, and then to an oxidative aromatization reaction to obtain a compound of the general formula D:

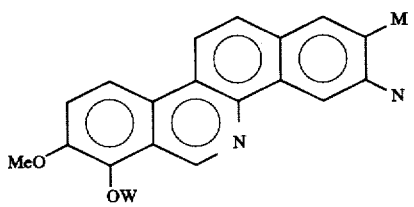

wherein M and N individually represent a hydroxyl or lower alkoxy group, or M and N simultaneously represent a hydrogen atom or together form a methylenedioxy group; and W represents a protective group, and that the compound D thus formed is reacted with an N-alkylating agent to effect an N-alkylation of said compound; and that the N-alkylated compound thus formed is subjected to a protective group-removing operation and treated with an acid to form the aimed salt type product.

The invention also provides a pharmaceutical composition for the use as an antitumor agent comprising, as an effective ingredient, a novel benzo[c]phenanthridinium derivative of the general formula A:

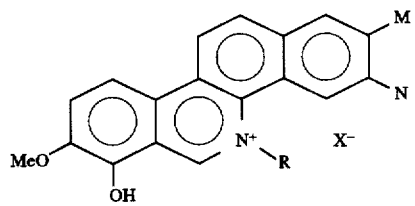

wherein M and N individually represent a hydroxyl or lower alkoxy group, or M and N simultaneously represent a hydrogen atom or together form a methylenedioxy group; X⁻ represents an acid residue or a hydrogen acid residue; and R represents a lower alkyl group.

The hydrogen salts of the compounds according to the invention have excellent stability, and therefore they have an advantage in formulating a pharmaceutical preparations thereof.

As examples of lower alkoxy groups, there may be mentioned $C_1$–$C_5$ alkoxy groups such as methoxy, ethoxy, n-propoxy, i-propoxy, n-butoxy, i-butoxy, t-butoxy and pentoxy groups and the like. Preferred are $C_1$–$C_3$ alkoxy groups such as methoxy, ethoxy n-propoxy and i-propoxy groups. Examples of lower alkyl groups are $C_1$–$C_5$ alkyl groups such as methyl, ethyl, n-propyl, i-propyl, n-butyl, i-butyl, t-butyl and pentyl groups, etc. Preferred are $C_1$–$C_3$ alkyl groups such as methyl, ethyl, n-propyl and i-propyl groups.

The acid residues means normal salt-forming acid residues, including inorganic acid residues such as halide ions, e.g., chloride ion Cl⁻, bromide ion Br⁻, iodide ion I⁻, fluoride ion F⁻, etc., and also including sulfate ion $SO_4^{2-}$, nitrate ion $NO_3^-$, nitric ions, phosphatic ions, sulfuric ions, etc., residues of organic acids such as p-toluenesulfonate ion TsO⁻, dimethylsulfate, diethylsulfate, etc.; and the hydrogen acid residue means hydrogen salt-forming acid residues which have one or two hydrogen atoms, for instance, hydrogen sulfate ion $HSO_4^-$, dihydrogen phosphate ion $H_2PO_4^-$ and the like. In order to increase the stability of the present compounds, it is preferred to use hydrogen salt-forming acid residues represented by $HnX_a^-$ (n means 1 or 2, $X_a^-$ means $SO_4^-$ or $PO_4^-$) including, for instance, hydrogen sulfate ion, dihydrogen phosphate ion and the like.

The compounds of the general formula C are novel compounds and may be prepared for instance, in a manner shown below.

The starting material is 2,3-dihydroxy-5-nitronaphthalene which is a known compound [Collection Czechoslovak. Chem. Commun., 53, 3184 (1988)]. The starting material is converted into a nitronaphthalene compound of the formula F:

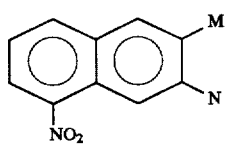

wherein M and N individually represent a hydroxyl or lower alkoxy group, or M and N together form a methylenedioxy group.

Then, the compound of the formula F is reduced to a compound of the formula B:

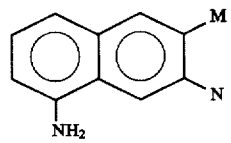

wherein M and N individually represent a hydroxyl or lower alkoxy group, or M and N simultaneously represent a hydrogen atom or together form a methylenedioxy group. The 5-amino naphtalene, a compound of the formula B, is a known compound and is commercially available (Merk Index, 10, 6250).

The naphthylamine of formula B is condensed with 2-(protected hydroxy)-3-methoxy-6-halogenobenzaldehyde under dehydration conditions to form a condensation product which is a Schiff's base. Thereafter, the Schiff's base is selectively reduced so as to obtain the compound of formula C.

Next, a more detailed explanation will be made on the process mentioned above.

1. Synthesis of compounds of the general formula F

Compounds of the general formula F, wherein M and N together form a methylenedioxy group, can be produced by a process, wherein 2,3-dihydroxy-5-nitronaphthalene is dissolved in a non-aqueous polar solvent such as dimethyl formamide or the like, and then reacted under heating at a temperature of from 60° to 110° C. with a dihalogenomethane, preferably dichloromethane or dibromomethane, in the presence of a fluoride salt, preferably cesium fluoride or potassium fluoride as catalyst, to obtain 2,3-(methylenedioxy)-5-nitronaphthalene (compound 1).

In the case of compounds of the general formula F, wherein M and N individually represent a hydroxyl or lower alkoxy group, such compounds may be prepared by a process, wherein 2,3-dihydroxy-5-nitronaphthalene is dissolved in a non-aqueous polar solvent such as dimethyl formamide or the like, and then alkylated by reacting with an alkyl halide such as methyl iodide, ethyl iodide, isopropyl bromide or the like, in the presence of an alkaline catalyst, for instance, $Li_2CO_3$ or $K_2CO_3$ at a temperature of from 50° to 100° C. for 10 to 20 hours. When 1 mol of alkyl halide is reacted with the 2,3-dihydroxy-5-nitronaphthalene, two kinds of monoalkoxy compounds will be obtained. For the production of dialkoxy compounds, use should preferably be made of at least 2 mol of alkyl halides. If it is desired to produce a lower alkoxy-substituted compound, wherein N and M are different from each other, then a process may be conducted, wherein a monoalkoxy compound, which has been isolated by means of a fractionation, is further reacted with an alkyl halide.

2. Synthesis of compounds having the general formula B

Compounds of the general formula B can be obtained by reducing the nitro group of compounds, having the general formula F, to an amino group. For carrying out this reaction, it is possible to use any reducing agents customarily employed in reducing a nitro group to an amino group. A preferred method comprises heating the reactant in ethanol in the presence of a 5 or 10% palladium/carbon catalyst under reflux.

2,3-methylenedioxy-5-aminonaphthalene may also be obtained by a known process described in J. Org. Chem., 53, 1708 (1988), although said known process has many steps, and produces the aimed compound in a low yield.

3. Synthesis of compounds having the general formula C

For this synthesis naphthylamine compounds of the general formula B are reacted with 2-(protected oxy)-3-methoxy-6-halogenobenzaldehyde (which can be produced by a known method described, for instance, in J. C. S. Perkin I, 1221 (1976) and J. Org. Chem., 53, 1708(1988) by heating the reactants in toluene or benzene to a temperature of from 80° to 110° C. for 1–3 hours and then by concentrating the reaction mixture in such a manner that the water, which has been produced as by-product by the condensation of the amino group with the aldehyde group, is effectively removed from the reaction system by an azeotropic distillation with toluene or benzene. It is preferred that, after the concentration, the resulting residue is admixed with fresh toluene or benzene, and then again subjected to a heating/concentration operation. By repeating 2–4 times the heating/concentration operation, it is possible to obtain a dehydrated condensate product (Schiff's base) in a substantially quantitative yield.

Then, the double bond of the condensed portion of the dehydrated condensate product is subjected to a reducing reaction to form the aimed compounds of the general formula C. In carrying out the reducing reaction, use may be made of any reducing agents which can reduce a CN double bond. Preferably, this reaction is performed in the presence of sodium cyanoborohydride or dimethylamine borone as reducing agent at a low reaction temperature of from −10° to 40° C.

Next, the detailed processes of the present invention are explained.

A. Synthesis of compounds having the general formula D

A compound of the general formula C is subjected to a ring closure reaction (condensation reaction by elimination of hydrogen halide) in the presence of organic tin hydrides in an organic solvent. The preferable organic tin hydrides are tri-hydrocarbon $(C_1-C_{10})$tin hydrides, e.g. tri-n-octyltin hydride, triphenyltin hydride, tri-n-butyltin hydride, tri-ethyltin hydride or trimethyltin hydride, or di-hydrocarbon $(C_1-C_6)$tin hydrides e.g. diphenyltin hydride or di-n-butyltin hydride. In general, tri-n-butyltin hydride and tri-n-octyltin hydride are more preferable, and usually used. In carrying out this reaction, 1–6 equivalents, preferably 2–3 equivalents of organic tin hydride are dissolved in an organic solvent, preferably $C_6-C_{10}$ hydrocarbon solvent, for example toluene, xylen or benzene, and preferably admixed with a radical reaction initiator such as 2,2'-azobis (isobutyronitrile), 2,2'-azobis(2-methylbutyronitrile), 2,2'-azobis(2,4-dimethylvaleronitrile), benzoyl peroxide or the like. The reaction mixture is heated to a temperature of from 60° to 150° C., preferably 80° to 130° C. for 2 minutes to 4 hours, preferably 5 minutes to 1 hour to complete the ring closure reaction. Thereafter, preferably without separating the condensation product from reaction mixture, an oxidative aromatization reaction of the closed ring is carried out in the presence of an oxidizing agent at a temperature between 0° and 100° C. preferably 10° and 40° C. for 1 to 120 minutes, preferably 5 to 50 minutes, to obtain the compound of the general formula D.

Various oxidizing agents can be used for this reaction, and include, for example, manganese dioxide, lead tetraacetate, mercury acetate and dichloro dicyanobenzoquinone (DDQ), preferably active manganese dioxide.

By the above-mentioned reactions, the skeletons of benzo [c]phenanthridine will be formed.

As the halogen atom in the general formula C, use is generally made of a bromine atom. Referring to the protective groups W in the general formulas C and D, any kinds of protective groups for hydroxyl groups may be employed without any specific limitations, for example, acyl $(C_2-C_8)$ groups such as acetyl and benzoyl, and $C_1-C_6$ alkyl carbonyl and $C_3-C_{10}$ hydrocarbon groups such as branched alkyl $(C_3-C_6)$ groups and substituted or unsubstituted benzyl. The preferable protective groups are benzyl series protective groups such as substituted or unsubstituted benzyl groups, or branched alkyl $(C_3-C_5)$ groups.

B. Synthesis of compounds having the general formula A

A benzo[c]phenanthridine compound of the general formula D is subjected to an N-alkylation reaction, then the protective groups are removed from the compound, and thereafter an acid treatment is conducted to produce a benzo[c]phenanthridinium derivative of the general formula A.

In effecting the N-alkylation, the compound of the general formula D and an alkylating agent may be dissolved in an organic solvent, for example, $C_6-C_{10}$ hydrocarbon solvent such as dry toluene, dry benzene, dry xylene or the like, or may be used in the absence of any solvents. These reactants are heated in the absence of catalysts or in the presence of salts such as alkali-metal halogenides or carbonates, preferably potassium bromide, anhydrous potassium carbonate, anhydrous sodium carbonate and the like.

The reaction temperature is usually 50° to 180° C., preferably 100° to 150° C. The reaction time is usually 1–48 hr, preferably 2 to 24 hr.

As the alkylating agents for the above reaction, use may be made of any of conventional agents customarily employed for N-alkylation reactions of pyridine rings. Examples of preferred alkylating agents include lower ($C_1$–$C_4$)alkyl sulfonates used for an alkylation such as lower alkyl substituted benzenesulfonate (for example, lower alkyl p-toluenesulfonates, and more highly reactive agents such as lower alkyl 2,4-dinitro-benzenesulfonates and lower alkyl 2-nitrobenzenesulfonates) or lower alkyl trihalogenomethane sulfonates. The alkylating agents are, for example, methyl p-toluenesulfonate, ethyl 2,4-dinitrobenzenesulfonate, methyl 2-nitrobenzenesulfonate, n-propyl 2-nitrobenzenesulfonate and methyltrifluoromethane sulfonate.

The protective group removal operation is carried out in consideration of the kinds of the protective groups to be removed. For instance, in the case of benzyl series protective groups or isopropyl group, such groups may be removed by heating at 60° to 150° C., preferably 80° to 120° C. under acidic conditions, e.g. in the presence of hydrochloric acid. The reaction time is usually 0.1 to 10 hr preferably 0.5 to 3 hr.

After the protective groups have been removed from the compound, an acid treatment of the compound is carried out, for instance, in a manner, wherein the compound is dissolved in a small amount of a polar solvent such as methanol or the like, and then admixed with an acid, for example, hydrochloric acid, sulfuric acid or p-toluenesulfonic acid diluted with water. The pH of the solution must be below pH 4. An amount of an acid is usually about 1 to 3 mols per 1 mol of the compound. Furthermore, an organic solvent such as acetone, which is highly miscible with water, is added to the reaction solution to form salts as precipitates, and the reaction solution is dried, so that the compound of the general formula A is obtained as yellow powder.

When $X^-$ is an acid ion having a valency of at least two, for instance, a sulfate ion, it is necessary to decrease the amount of sulfuric acid to be added. If sulfuric acid is used in a molar amount 1.0–2.5 times larger than the quantitative amount, then a hydrogen sulfate salt (wherein $X^-$ is $HSO_4^-$) will be formed. If sulfuric acid is employed in a half amount, then a normal type sulfate salt (wherein $X^-$ is ½ $SO_4^{2-}$) will be formed.

The compounds according to the invention have characteristic chemical properties as explained below. When the benzo[c]phenanthridinium derivatives of the general formula A is treated with a base, then compound will release 1 equivalent of the acid from the molecule. Therefore, it is considered that the compound may also has a form with an intramolecular zwitterion structure represented by the following formula E:

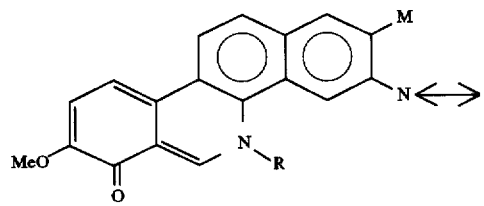

(E)

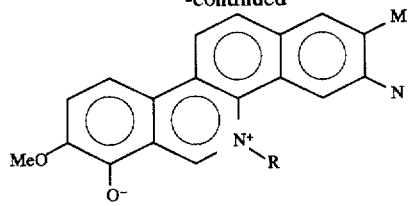

wherein M and N individually represent a hydroxyl or lower alkyl group, or M and N simultaneously represent a hydrogen atom or together form a methylenedioxy group; and R represents a lower alkyl group.

Alternatively, the compounds of the general formula E may also be treated with acids to convert them into the compounds of the general formula A. The quaternary salt structure represented by the general formula A is present in the solution having below pH about 4, while the intramolecular salt structure represented by the general formula E is present in the solution having higher than pH about 4. Therefore, the compound of formula A can be obtained when the compound is precipitated from the solution of which the pH is below about 4.

As for the stability of the salt type compounds according to the invention, the acidic salts (i.e. hydrogen salts: $X^-$ represents hydrogen acid residue), which still contain protons (hydrogen atoms), have a resistance to foreign basic materials. Therefore, the acidic salts are more stable than the normal salts containing no protons.

For example, even in the case of 2,3-(methylenedioxy)-5-methyl-7-hydroxy-8-methoxy-benzo[c]phenanthridinium chloride which seems to have relatively good properties (stability), there is a problem that, when it is stored at room temperature for a long period of time, it will be gradually decomposed. This compound is a powdery material having a yellowish color immediately after the production thereof. It gradually changes its color into brown. After 3 months from the production thereof, the compound has a dark blackish brown color and also has properties different from those initially observed. This is because a decomposition product, which is difficultly soluble in water, has been formed during the storage of the compound. So, it is not considered that the compound has properties suitable for formulating into a pharmaceutical preparation.

2,3-(methylenedioxy)-5-methyl-7-hydroxy-8-methoxy-benzo[c]phenanthridinium hydrogen sulfate (compound A-0), wherein the acid residue $X^-$ is a hydrogen sulfate ion $HSO_4^-$, is a compound according to the invention, and can be obtained as yellow powder. When this compound is stored at room temperature for 1 month, there is no change in its color, and therefore the compound is virtually different in this point from the above-mentioned chloride compound, wherein the acid residue $X^-$ is a chloride ion $Cl^-$. Furthermore, there are observed no color change and no decomposition in the case of the compound according to the invention having a form of yellow powder, even after it has been stored for 3 months from the production thereof. A 0.5 µM aqueous solution of 2,3-(methylenedioxy)-5-methyl-7-hydroxy-8-methoxy-benzo[c]phenanthridinium chloride, wherein the acid residue $X^-$ is a chloride ion $Cl^-$, has a pH of 4.3. On the other hand, a 0.5 µM aqueous solution of 2,3-(methylenedioxy)-5-methyl-7-hydroxy-8-methoxy-benzo[c]phenanthridinium hydrogen sulfate according to the invention, wherein the acid residue $X^-$ is a hydrogen sulfate ion $HSO_4^-$, has a pH of 3.9. Thus, the hydrogen sulfate compound has a lower pH, and therefore it is recognized that said compound has a higher resistance to foreign basic materials and is more stable accordingly. There are no disadvantages in the pharmaceutical activities of such compounds when they have the form of hydrogen salts such as hydrogen sulfate. Therefore, the hydrogen salt compounds are practically useful as medicines in view of the enhanced stability thereof.

The compounds of formula A in accordance with the present invention have an excellent antitumor activity as will be later shown in pharmacological tests. The compounds exert a remarkable growth inhibition activity on various tumor cells cultured. Furthermore, the compounds of the present invention inhibit growth of tumor in various animals with tumor and exhibit a prolongation of increased life span. In addition, the compounds inhibit platelet aggregation due to platelet activated factor and inhibit metastasis of tumor. Therefore, the antitumor composition of the present invention is effective for solid tumors of human, for example, gastric cancer, liver cancer, rectal cancer, lung cancer, etc.; and for blood diseases such as leukemia, Hodgkin's disease, etc.

When the compounds of formula A in accordance with the present invention are used as drugs, the compounds may be prepared into pharmaceutical preparations and the preparations may be applied in various conventional manners. That is, the preparations may be applied parenterally, orally, intrarectally, etc. The preparations may take the form of an injection, powder, a granulate, a tablet, a suppository, etc. In preparing the pharmaceutical composition, a variety of auxiliary agents used in drugs, namely, carrier and other aids, for example, a stabilizer, an antiseptic, a pain killer, an emulsifying agent, etc. may be used, if necessary and desired.

In the composition, the content of the compound shown by formula A may be varied over a wide range depending upon form of preparation, but the composition may contain generally in an amount of 0.01 to 100% by weight, preferably 0.1 to 50% by weight, of the compound shown by formula A. The balance is a carrier and other auxiliary agents used for conventional drug compositions.

A does of the compound of formula A varies depending on condition, etc., but is generally approximately 50 to 500 mg per day for adult.

Next, representative examples of benzo[c] phenanthridinium derivatives of the general formula A are shown in Table 1. However, it should be noted that the compounds according to the invention are not limited only to those shown in the table.

TABLE 1

| Compound No. | Compound |
| --- | --- |
| A-0 | 2,3-(Methylenedioxy)-5-methyl-7-hydroxy-8-methoxybenzo[c]phenanthridinium salt |
| A-1 | 2,3-(methylenedioxy)-5-ethyl-7-hydroxy-8-methoxybenzo[c]phenanthridinium salt |
| A-2 | 2,3-(Methylenedioxy)-5-(n-propyl)-7-hydroxy-8-methoxy-benzo[c]phenanthridinium salt |
| A-3 | 2,8-Dimethoxy-3,7-dihydroxy-5-methyl-benzo[c]phenanthridinium salt |
| A-4 | 2,7-Dihydroxy-3,8-dimethoxy-5-methyl-benzo[c]phenanthridinium salt |
| A-5 | 2-Isopropoxy-3,8-dimethoxy-5-methyl-7-hydroxy-benzo[c]phenanthridinium salt |
| A-6 | 2,3,7-Trihydroxy-5-methyl-8-methoxy-benzo[c]phenanthridinium salt |
| A-7 | 5-Ethyl-7-hydroxy-8-methoxy-benzo[c]phenanthridinium salt |
| A-8 | 5-Methyl-7-hydroxy-8-methoxy-benzo[c]phenanthridinium salt |

Representative examples of the intermediate compounds, having the general formula D, are shown in Table 2.

TABLE 2

| Compound No. | Compound |
| --- | --- |
| D-1 | 2,3-(Methylenedioxy)-7-benzyloxy-8-methoxy-benzo[c]phenanthridine |
| D-2 | 2,3-(Methylenedioxy)-7-isopropoxy-8-methoxy-benzo[c]phenanthridine |
| D-3 | 2,8-Dimethoxy-3-isopropoxy-7-benzyloxy-benzo[c]phenanthridine |
| D-4 | 2-Isopropoxy-3,8-dimethoxy-7-benzyloxy-benzo[c]phenanthridine |
| D-6 | 2,3-Diisopropoxy-7-benzyloxy-8-methoxy-benzo[c]phenanthridine |
| D-7 | 7-Benzyloxy-8-methoxy-benzo[c]phenanthridine |

Representative examples of the intermediate compounds, having the general formula C, are shown in Table 3.

TABLE 3

| Compound No. | Compound |
| --- | --- |
| C-1 | N-[(2'-benzyloxy)-3'-methoxy-6'-bromobenzyl]-6,7-(methylenedioxy)-1-naphthylamine |
| C-3 | N-[(2'-benzyloxy)-3'-methoxy-6'-bromobenzyl]-6-methoxy-7-isopropoxy-1-naphthylamine |
| C-4 | N-[(2'-benzyloxy)-3'-methoxy-6'-bromobenzyl]-6-isopropoxy-7-methoxy-1-naphthylamine |
| C-6 | N-[(2'-benzyloxy)-3'-methoxy-6'-bromobenzyl]-6,7-diisopropoxy-1-naphthylamine |
| C-7 | N-[(2'-benzyloxy)-3'-methoxy-6'-bromobenzyl]-1-naphthylamine |

Test

Now, the Pharmaceutical Test Examples are shown. The benzo[c]phenanthridinium derivatives according to the invention have a growth inhibition activity against various cultured tumor cells as shown below. Furthermore, the derivatives also have an activity for inhibiting a blood platelet aggregation caused by platelet activating factors.

1. Growth inhibitory activity against tumor cells

Various tumor cells were cultured at 37° C. for 24 hours in 5% gaseous carbon dioxide, and then subjected to an action of a test drug for 2–4 days. After that, the cells were stained with 0.05% Methylene Blue. The pigment were extracted from the stained cells. The growth inhibition rate of the cells was determined based on absorbance of the extracted pigment at 660 nm, and the 50% growth inhibitory concentration ($IC_{50}$) was calculated. The test results are shown in Table 4.

TABLE 4

| Compound No. | A-0 ($X^- = HSO_4^-$) | A-1 ($X^- = HSO_4^-$) | A-2 ($X^- = HSO_4^-$) | A-3 ($X^- = Cl^-$) | A-4 ($X^- = Cl^-$) | A-6 ($X^- = OTs^-$) | A-7 ($X^- = HSO_4^-$) | A-8 ($X^- = HSO_4^-$) |
|---|---|---|---|---|---|---|---|---|
| | IC$_{50}$ (μg/ml) | | | | | | | |
| HeLa S$_3$ | 0.15 | 0.177 | n.t. | 3.0 | 0.201 | 2.1 | 0.69 | 0.26 |
| MMI | 0.12 | 0.165 | 0.273 | n.t. | 0.996 | n.t. | n.t. | 0.262 |
| SHIN-3 | 0.192 | 0.170 | 0.414 | n.t. | 1.06 | n.t. | n.t. | 0.155 |
| N-231 | 0.036 | 0.040 | 0.085 | n.t. | 0.199 | n.t. | n.t. | 0.062 |
| Lu-130 | 0.055 | 0.250 | 0.108 | n.t. | 0.291 | n.t. | n.t. | 0.051 |
| Nakajima | n.t. | 0.426 | 0.777 | n.t. | 1.87 | n.t. | n.t. | n.t. |

In this table, the abbreviated expressions have the following tumor cells: HeLa S3=cervical carcinoma; MMI=ovarian cancer; SHIN-3=ovarian cancer; N-231=small cell lung cancer; Lu-130=small cell lung cancer; Nakajima=gastric cancer; and the expression "n.t." represents "not tested". These tests were conducted according to a simultaneous comparison test method, except the case of HeLa S$_3$.

2. Inhibition activity on platelet aggregation

Platelet-rich plasma (PRP) was collected from Japanese albino rabbits (weighing 3–4 kg). As a platelet aggregation inducer, platelet activating factor (PAF) was used in a final concentration of $10^{-7}$M. A test drug was added to PRP. After incubation for a definite period of time, PAF was added to cause a platelet aggregation reaction. The reaction was terminated with EDTA. After a centrifugation, the supernatant was removed to obtain platelet precipitates. Distilled water was added to the platelet precipitates, whereby the serotonin remained in the platelet was reacted with an orthophthalaldehyde reagent to form a serotonin-orthophthaladehyde condensate. The condensate was measured at an excited wavelength of 360 nm and at a measurement wavelength of 475 nm. Anti-PAF activity of the test drug was determined by the following equation.

Serotonin release inhibition rate (%) =

$$\frac{(\text{Test drug} + PAF)\text{value} - PAF \text{ value}}{\text{Blank value} - PAF \text{ value}} \times 100$$

In the equation, the expression "value" stands for "serotonin value".

The test results of several compounds are shown in Table 5.

TABLE 5

| Test drug (Compound No.) | Concentration (μg/ml) | Inhibition rate (%) |
|---|---|---|
| A-1 ($X^- = HSO_4^-$) | 100 | 96.5 |
| | 50 | 74.1 |
| | 25 | 49.6 |
| | 12.5 | 25.2 |
| A-8 ($X^- = HSO_4^-$) | 100 | 46.4 |
| | 50 | 26.5 |
| | 25 | 10.9 |
| Physiological saline | — | 0.0 |

As is clear from Table 5, the test drugs showed a potent inhibition activity on platelet aggregation.

3. Antitumor Effect in vivo Against Tumor Human Cells

In the following example, Compound No. A-0 ($X^-=HSO_4^-$) was used.

Human large cell lung tumor (LX-1), human glioma (SC-2) and human liver tumor (Li-7) were subcutaneously transplanted, respectively, at the side abdomen of nude mouse (BALB/c-nu). From the day when the tumor volume reached 50–100 mm$^2$, the test drug was dissolved in 5% glucose aqueous solution and the solution was administered from the tail vein of said mouse 3 times once a day every 4 other days (q4d×3) in a dose of 100 mg/kg.

The antitumor effect was judged from a mean tumor growth value (LW2/2) obtained by measuring a long-size diameter (L) and a short-size diameter (W) of the tumor. The test using no drug was made as control.

The results obtained are as shown in Tables 6, 7 and 8. As is apparent from these results, the test compound No. A-0 ($X^-=HSO_4^-$) showed a strong antitumor effect against the three types of tumors.

TABLE 6

Effect on Human lung large cell tumor LX-1

| | Mean tumor growth value (LW$^2$/2) | | | | | |
|---|---|---|---|---|---|---|
| | 1 | 4 | 9 | 14 | 21 | 25 (day) |
| Compound A-0 ($X^- = HSO_4^-$) 100 mg/kg (q4d × 3) (n = 5) | 1.0 | 1.6 | 1.5 | 1.3 | 2.7 | 5.1 |
| Control (n = 7) | 1.0 | 1.9 | 4.2 | 9.0 | 12.1 | 15.5 |

TABLE 7

Effect on human glioma SC-2

| | Mean tumor growth value (LW$^2$/2) | | | | | | |
|---|---|---|---|---|---|---|---|
| | 1 | 5 | 12 | 19 | 25 | 32 | 40 (day) |
| Compound A-0 ($X^- = HSO_4^-$) 100 mg/kg (q4d × 3) (n = 5) | 1.0 | 1.4 | 1.2 | 1.5 | 3.2 | 10.4 | 22.3 |
| Control (n = 5) | 1.0 | 1.7 | 5.2 | 15.6 | 27.4 | 43.3 | 70.6 |

TABLE 8

Effect on human liver tumor Li-7

| | Mean tumor growth value (LW²/2) | | | | |
|---|---|---|---|---|---|
| | 1 | 2 | 9 | 11 | 14 (day) |
| Compound A-0 (X⁻ = HSO₄⁻) 60 mg/kg (q4d × 3) (n = 5) | 1.0 | 1.5 | 2.0 | 1.4 | 2.1 |
| Control (n = 6) | 1.0 | 2.3 | 10.0 | 16.6 | DEAD |

4. Acute toxicity

In the acute toxicity test, the compounds according to the invention were intravenously administered to female $CDF_1$ mice of 6 weeks age. The mice survived in a dose of 100 mg/kg without showing any lethal toxicity.

From the test data shown above, it can be said that the benzo[c]phenanthridinium derivatives of the general formula A according to the invention have not only an antitumor activity against various tumor cells, but also an inhibition activity on platelet aggregation, the latter activity being considered to have a relation with an activity for inhibiting a metastasis of cancer. So, it is expected that the compounds according to the invention may be effectively used as drugs for the treatment of cancer. When the compounds according to the invention are used in the form of salts, it is advantageous to use hydrogen salts of the compounds for the reason that the hydrogen salts of the compounds serve to enhance the stability of pharmaceutical preparations containing the compounds.

Hereinafter pharmacological tests and examples are shown below using 7-hydroxy-8-methoxy-5-methyl-2,3-methylenedioxybenzo[c]phenanthridinium chloride, but the present invention is not to be deemed limited thereto.

1. Growth inhibition test on tumor cells in vitro

Experimental conditions for each cell are shown in Table A. After the test drug was exposed for 2 to 4 days on each cell cultured at 37° C. for 24 hours in 5% $CO_2$ under the conditions, the cells were stained with 0.05% Methylene Blue. The pigment was extracted from the stained cells. A growth inhibition rate of the cell was determined based on absorbance of the extracted pigment at 660 nm and 50% growth inhibitory concentration ($IC_{50}$) was calculated.

TABLE A

Culture Condition for Various Tumor Cells

| Cell | Count of Cell Inoculated | Time for Incubation |
|---|---|---|
| Hela S₃ | 7.5 × 10³/ml | 72 hours |
| Colon 26 | 7.5 × 10³/ml | 65 hours |
| SW1116 | 1.5 × 10⁴/ml | 96 hours |
| Li-7 | 1.5 × 10⁴/ml | 48 hours |
| HepG2 | 1.0 × 10⁴/ml | 96 hours |
| LL | 4.0 × 10³/ml | 72 hours |
| PC-3 | 1.0 × 10⁴/ml | 72 hours |
| B16 | 7.5 × 10³/ml | 72 hours |

As a comparative examples, chelerythrine (7,8-dimethoxy-5-methyl-2,3-methylenedioxybenzo[c]phenanthridinium chloride) is tested.

The results are shown in Table B. As is obviously noted from Table B, the test drug inhibited the growth of various tumor cells.

TABLE B

Cell Growth Inhibition Activity Against Various Tumor Cells ($IC_{50}$ (μg/ml))

| Kind of Cell | Test Drug | Chelerythrine |
|---|---|---|
| Hela S₃ | 0.32 | 2.0 |
| Colon 26 | 0.038 | N.T. |
| SW1116 | 0.25 | 2.1 |
| Li-7 | 0.12 | 0.47 |
| HepG2 | 0.059 | N.T |
| LL | 0.044 | N.T |
| PC-3 | 0.21 | 2.0 |
| B16 | 0.057 | N.T |

(N.T.; not tested)

2. Antitumor Activity against Tumors Cell in vivo
Antitumor activity in vivo (1)

Three kinds of mouse leukemia P388, fibrosarcoma M5076 and colon 26 adenocarcinoma C26 were used. P388 (10⁶/mouse) and C26 (10⁵/mouse) were intraperitoneally or subcutaneously transplanted to female $CDF_1$ mice (5 mice per one group) of 6 weeks age. M5076 (10⁶/mouse) was subcutaneously transplanted to female C57BL/6 mice (5 mice per one group) of 6 weeks age. The test drug was dissolved in 20% dimethylsulfoxide upon use; the solution was intraperitoneally administered to the P388 group and the M5076 group once a day for consecutive 5 days from the next day following the transplantation of tumor. The solution was intraperitoneally administered to the C26 group once a day for consecutive 5 days from Day 5 after the transplantation of tumor. An antitumor activity was judged by a rate (T/C %) of the median in the number of survival dates in each group to that in the control group.

The results are shown in Tables C, D and E. As is clear from Tables C, D and E, the compound exerted a potent antitumor activity on the three kinds of tumor.

TABLE C

Effect on Leukemia P388

| | Dose (mg/kg/day) | Median Survival Time (day) | Effect (T/C %) |
|---|---|---|---|
| Test Drug | 25 | 22.5 | 223 |
| | 12.5 | 16.5 | 163 |
| | 6.25 | 14.8 | 147 |
| | 3.13 | 13.5 | 134 |
| Group administered with physiological saline | — | 10.1 | 100 |

TABLE D

Effect on Fibrosarcoma M5076

| | Dose (mg/kg/day) | Median Survival Time (day) | Effect (T/C %) |
|---|---|---|---|
| Test Drug | 25 | 28.5 | 154 |
| | 12.5 | 20.5 | 111 |
| | 6.25 | 20.5 | 111 |
| Group administered with physiological saline | — | 18.5 | 100 |

TABLE E

Effect on Colon Cancer C26

| | Dose (mg/kg/day) | Median Survival Time (day) | Effect (T/C %) |
|---|---|---|---|
| Test Drug | 50 | 42.5 | 139 |
| | 25 | 31.3 | 103 |
| | 12.5 | 33.5 | 110 |
| Group administered with physiological saline | — | 30.5 | 100 |

Antitumor Activity in vivo (2)
(a) Mouse colon tumor

Mouse colon 26 adenocarcinoma ($10^5$/mouse) was subcutaneously transplanted to female $CDF_1$ mice (3 mice per one group) of 6 weeks age. The test drug was intravenously administered once a day for consecutive 5 days from Day 7 after transplantation of the tumor at a dose of 50 mg/kg; or intravenously administered 3 times once a day every 4 other days in a dose of 75 mg/kg.

(b) Mouse lung tumor

Mouse lung tumor Lewis Lung ($10^6$/mouse) was subcutaneously transplanted to male $BDF_1$ mice (3 mice per one group) of 6 weeks age. The test drug was intravenously administered 3 times once a day every 4 other days at a dose of 60 mg/kg on Day 8 after the transplantation.

(c) Human liver tumor

Human liver Cancer Li-7 (fragment) was subcutaneously transplanted to female nude BALB-c/nu-A mice (3 mice per one group) of 6 weeks age. The test drug was intravenously administered 3 times once a day every 4 other days at a dose of 60 mg/kg on Day 8 after the transplantation.

In (a), (b) and (c) described above, the antitumor activity was determined by a ratio (T/C %) of the administered group to the control group in the number of day until a size of the tumor became 10 times that at the time when the administration started and increased life span of mice (T/C %). The results are shown in Table F. The results reveal that the compound inhibit growth of C26, LL and Li-7 tumors and its increased life span shows as high as 130% or more in the mice with any of the tumors.

TABLE F

| Tumor Cell | Test Compound Dose (mg/kg) | Schedule | Rate of tumor growth delay (%) | Increased Life Span (T/C %) |
|---|---|---|---|---|
| C26 | 50 | g1d × 5 | 219 | 135 |
| C26 | 75 | g4d × 3 | 203 | 135 |
| LL | 75 | g4d × 3 | 118 | 152 |
| Li-7 | 60 | g4d × 3 | 253 | 137 |

3. Inhibition activity on platelet aggregation

Platelet-rich plasma (PRP) was collected from Japanese albino rabbits (weighing 3–4 kg). As a platelet aggregation inducer, platelet activating factor (PAF) was used in a final concentration of $10^{-7}$M. The test drug was added to PRP. After incubation for a definite period of time, PAF was added to cause platelet aggregation reaction. The reaction was terminated with EDTA. After the centrifugation, the supernatant was removed to obtain the platelet pellet. Distilled water was added to the platelet precipitates, whereby serotonin remained in platelet was reacted with orthophthalaldehyde reagent to form sertonin-orthophthalaldehyde condensate. The condensate was measured at an excited wavelength of 360 nm and at a measurement wavelength of 475 nm. Anti-PAF activity of the test drug was determined by the following equation.

Serotonin release inhibition rate (%) =

$$\frac{(\text{Test drug plus } PAF) \text{ value} - PAF \text{ value}}{\text{Blank value} - PAF \text{ value}} \times 100$$

The result is shown in Table G. As is clear from Table G, the test drug showed a potent inhibition activity on platelet aggregation.

TABLE G

Inhibition Activity on Platelet Aggregation

| | Concentration (μg/ml) | Inhibition Rate (%) |
|---|---|---|
| Test Drug | 100 | 107 |
| | 50 | 107 |
| | 25 | 85.5 |
| | 12.5 | 48.6 |
| Physiological saline | — | 0.0 |

4. Inhibition Activity of Tumor Metastasis in vivo

The test drug was intraperitoneally administered to male C57BL/6 mice of 5 weeks age at a dose of 25 or 50 mg/kg. Fifteen minutes after, highly metastatic mouse melanoma B16BL6 ($10^5$/mouse) was transplanted to mice through the tail vein. After mice were bred to death on Day 14 after the transplantation, the number of metastasis of BL6 into the lung was visually observed.

As is clear from Table H, the test drug inhibited metastasis of melanoma into the lung.

TABLE H

Inhibition Activity of Tumor Metastasis in vivo

| | Dose (mg/kg) | Number of Metastatic Node (mean + S.E.) |
|---|---|---|
| Test Drug | 50 | 76.9 ± 13.6 |
| | 25 | 55.8 ± 15.7 |
| Physiological saline | — | 111.9 ± 19.8 |

5. Acute toxicity

The test drug was intravenously administered to female $CDF_1$ mice of 6 weeks age. The mice survived in a does of 100 mg/kg without showing any lethal toxicity.

The foregoing results reveal that 7-hydroxy-8-methoxy-5-methyl-2,3-methylenedioxybenzo[c]phenanthridinium chloride of the present invention exhibits an antitumor activity and inhibition activity of platelet aggregation, and is thus expected as a useful agent for the treatment of tumors.

Now, a detailed explanation will be made about the production of several representative benzo[c] phenanthridinium derivatives having the general formula A, by the Examples shown below. However, it should be noted that the scope of the invention is not restricted only to these Examples.

EXAMPLE 1

Synthesis of 2,3-(methylenedioxy)-5-nitronaphthalene (compound 1)

19.3 g (0.094 mol) of 2,3-(dihydroxy)-5-nitronaphthalene as the starting material and 71.5 g (0.47 mol) of cesium fluoride were added to 290 ml of dry dimethyl formamide. The resulting mixture was stirred to form a solution. The solution was admixed with 6.63 ml (0.103 mol) of dichloromethane, and heated to 110° C. After that, the operation of adding the same amount of dichloromethane was repeated four times at an interval of 1 hour, and then the reaction mixture was heated for 2 hours to complete the reaction. After cooling, the reaction mixture was diluted with water, and extracted with diethyl ether. The extract solution was dried over anhydrous sodium sulfate, filtered, and concentrated. The resultant residue was recrystallized from ethyl acetate, so that 10.7 g of the first crystals and 1.82 g of the second crystals were obtained. Furthermore, the mother liquor was concentrated and refined by a silica gel column chromatography, wherein use was made, as eluent, of a petroleum ether-ethyl acetate mixture (9:1), whereby 2.00 g of the crystalline material was obtained. The total amount of compound 1 formed was 14.55 g (yield: 71%).

Compound 1: yellow powder.

$^1$H-NMR(200 MHz), DMSO-$d_6$, ppm: 6.26 (s, 2H), 7.52 (t, J=8.0 Hz, 1H), 7.58 (s, 1H), 7.74 (s, 1H), 8.55 (br d, J=8.0 Hz, 2H).

EXAMPLE 2

Synthesis of 2,3-(methylenedioxy)-5-naphthylamine (compound 2)

4.687 g (0.0216 mol) of compound 1 were dissolved in 200 ml of ethanol. The resulting solution was admixed with 10 ml of hydrazine hydrate and 1 g of a 5% palladium/carbon catalyst, and heated under reflux for 80 minutes. After cooling, the palladium/carbon catalyst was filtered off, and the filtrate was concentrated. The crude crystalline material thus formed was refined by a silica gel column chromatography, wherein use was made, as eluent, of a petroleum ether-ethyl acetate mixture (1:2), so that 3.566 g of compound 2 was obtained (yield: 88%).

Compound 2: light yellowish brown powder.

$^1$H-NMR(200 MHz), DMSO-$d_6$, ppm: 6.07 (s, 2H), 5.44 (br s, 2H), 6.54 (dd, J=7.2 & 1.5 Hz, 1H), 6.92 (br d, J=8.0 Hz, 1H), 7.02 (dd, J=8.0 & 7.2 Hz, 1H), 7.12 (s, 1H), 7.47 (s, 1H).

EXAMPLE 3

Synthesis of N-[(2'-benzyloxy)-3'-methoxy-6'-bromobenzyl]-6,7-(methylenedioxy)-1-naphthylamine (compound C-1)

3.548 g (18.95 mmol) of compound 2 and 6.304 g (19.63 mmol) of 2-(benzyloxy)-3-methoxy-6-bromobenzaldehyde were dissolved in 100 ml of toluene. The resulting solution was heated to 110° C. for 1 hour, and then concentrated under reduced pressure in a rotary evaporator. The residue thus obtained was admixed with 80 ml of fresh toluene, and the resulting mixture was heated for 1 hour, and then concentrated under reduced pressure in the same manner as above. The resultant residue (Schiff's base) was admixed with 50 ml of toluene, and cooled in an ice water bath. Then, a solution of 1.31 g (20.85 mmol) of sodium cyanoborohydride in 50 ml of methanol was dropwise added to the cooled solution under stirring over a period of 45 minutes. After 1 hour, the reaction mixture was admixed with water, and extracted with chloroform. The organic layer was dried over anhydrous sodium sulfate, then filtered and thereafter concentrated. The resulting residue was dissolved in a small amount of chloroform, and then admixed portionwise with the same quantity of petroleum ether to precipitate a crystalline material, which was then separated by filtration, and dried, so that 5.674 g of compound C-1 were obtained. The mother liquor was concentrated and refined by a silica gel column chromatography, wherein use was made, as eluant, of a petroleum ether-chloroform-ethyl acetate mixture (16:4:1), so that 1.415 g of compound C-1 was obtained. The total amount of compound C-1 formed was 7.089 g (yield: 76%).

Compound C-1: white powder.

$^1$H-NMR(200 MHz), CDCl$_3$, (ppm): 3.90 (s, 3H), 4.37 (br, 1H), 4.48 (s, 2H), 5.04 (s, 2H), 5.99 (s, 2H), 6.74 (dd, J=7.4 & 1.2 Hz, 1H), 6.82 (d, J=8.8 Hz, 1H), 7.05 (s, 1H), 7.07 (s, 1H), 7.11 (br d, J=8.0 Hz, 1H), 7.33 (d, J=8.8 Hz, 1H), 7.18–7.37 (m, 6H).

IR(KBr), (cm$^{-1}$): 3396, 3096, 3064, 3038, 2998, 2944, 2906, 2845, 1621, 1603, 1573, 1538(s), 1501, 1464(vs), 1435, 1400, 1393, 1371, 1316, 1285(s), 1271(s), 1251(s), 1218, 1202, 1194, 1173, 1144, 1131, 1099, 1072, 1040(s), 993, 960, 948, 916, 907, 862, 831, 795, 778, 757, 739, 687.

EXAMPLE 4

Synthesis of N-[(2'-benzyloxy)-3'-methoxy-6'-bromobenzyl]-6-methoxy-7-isopropoxy-1-naphthylamine (compound C-3)

463 mg of 2-methoxy-3-isopropoxy-5-naphthylamine and 707 mg of 2-(benzyloxy)-3-methoxy-6-bromobenzaldehyde were subjected to a reaction operation in a manner similar to that shown in Example 3. 970 mg of compound C-3 was obtained in a yield of 90%.

Compound C-3: white powder.

$^1$H-NMR(200 MHz), CDCl$_3$, (ppm): 1.36 (d, J=6.0 Hz, 6H), 3.88 (s, 3H), 3.94 (s, 3H), 4.53 (s, 2H), 4.57 (septet, J=6.0 Hz, 1H), 4.58 (br, 1H), 5.03 (s, 2H), 6.75 (dd, J=7.5 & 1.0 Hz, 1H), 6.80 (d, J=9.0 Hz, 1H), 7.08 (s, 1H), 7.09 (s, 1H), 7.13 (br d, J=7.5 Hz, 1H), 7.22 (t, J=7.5 Hz, 1H), 7.24–7.31 (m, 3H), 7.32 (d, J=9.0 Hz, 1H), 7.34–7.41 (m, 2H).

EXAMPLE 5

Synthesis of N-[(2'-benzyloxy)-3'-methoxy-6'-bromobenzyl]-6-isopropoxy-7-methoxy-1-naphthylamine (compound C-4)

463 mg of 2-isopropoxy-7-methoxy-5-naphthylamine and 481 mg of 2-(benzyloxy)-3-methoxy-6-bromobenzaldehyde were subjected to a reaction operation in a manner similar to that of Example 3 to obtain 800 mg of compound C-4 (yield: 99%).

Compound C-4: white powder.

$^1$H-NMR(200 MHz), CDCl$_3$, (ppm): 1.43 (d, J=6.0 Hz, 6H), 3.84 (s, 3H), 3.89 (s, 3H), 4.54 (s, 2H), 4.60 (br, 1H), 4.69 (septet, J=6.0 Hz, 1H), 5.04 (s, 2H), 6.76 (dd, J=7.5 & 1.0 Hz, 1H), 6.81 (d, J=9.0 Hz, 1H), 6.97 (s, 1H), 7.105 (s, 1H), 7.113 (br d, J=7.5 Hz, 1H), 7.22 (t, J=7.5 Hz, 1 h), 7.24–7.30 (m, 3H), 7.33 (d, J=9.0 Hz, 1H), 7.32–7.41 (m, 2H).

EXAMPLE 6

Synthesis of N-[(2'-benzyloxy)-3'-methoxy-6'-bromobenzyl]-6,7-diisopropoxy-1-naphthylamine (compound C-6)

406 mg of 2,3-diisopropoxy-5-naphthylamine and 707 mg of 2-(benzyloxy)-3-methoxy-6-bromobenzaldehyde were subjected to a reaction operation in a manner similar to that of Example 3 to obtain 756 mg of compound C-6 (yield: 89%).

Compound C-6: white powder.

¹H-NMR(200 MHz), CDCl₃, (ppm): 1.32 (d, J=6.1 Hz, 6H), 1.39 (d, J=6.1 Hz, 6H), 3.88 (s, 3H), 4.49 (septet, J=6.1 Hz, 1H), 4.51 (s, 2H), 4.55 (br, 1H), 4.61 (septet, J=6.1 Hz, 1H), 5.03 (s, 2H), 6.72 (dd, J=7.5 & 1.1 Hz, 1H), 6.80 (d, J=8.8 Hz, 1H), 7.08–7.40 (m, 10H).

IR(KBr), (cm⁻¹): 3420, 2978, 2936, 1626, 1595, 1581, 1522, 1468(s), 1437, 1383, 1334, 1277, 1253(s), 1215, 1182, 1159, 1139, 1112, 1079, 1012, 982, 954, 925, 860, 840, 800, 773, 735, 695.

EXAMPLE 7

Synthesis of N-[(2'-benzyloxy)-3'-methoxy-6'-bromobenzyl]-1-naphthylamine (compound C-7)

1.718 g of 5-naphthylamine and 4.239 g of 2-(benzyloxy)-3-methoxy-6-bromobenzaldehyde were subjected to a reaction operation in a manner similar to that of Example 3 to obtain 3.71 g of compound C-7 (yield: 62.7%).

Compound C-7: white powder.

¹H-NMR(200 MHz), CDCl₃, (ppm): 3.90 (s, 3H), 4.52 (s, 2H), 4.80 (br, 1H), 5.06 (s, 2H), 6.80–6.85 (m, 2H), 7.22–7.47 (m, 10H), 7.68–7.81 (m, 2H)

IR(KBr), (cm³¹ ¹): 3999(s), 3070, 2944, 2856, 1626, 1581(s), 1531, 1481, 1467(s), 1432, 1410, 1372, 1355, 1336, 1296, 1272(s), 1227, 1215, 1200, 1178, 1144, 1109, 1088, 1073(s), 983, 959, 911, 865, 795, 783, 764(s), 741, 690.

EXAMPLE 8-1

Synthesis of 2,3-(methylenedioxy)-7-benzyloxy-8-methoxybenzo[c]phenanthridine (compound D-1)

1.968 g (4 mmol) of compound C-1 and 2.91 g (10 mmol) of tributyltin hydride were dissolved in 100 ml of toluene, and the resulting solution was heated to 110° C. To this solution, 0.8 g of 2,2'-azobis(isobutyronitrile) were added. After 30 minutes, the reaction solution was cooled to room temperature, then admixed with 2 g of active manganese dioxide, and stirred for 20 minutes. Next, the manganese compound was separated off by filtration, and the filtrate was concentrated under reduced pressure. The residue thus obtained was passed through a silica gel column, wherein use was made, as eluant, of a chloroform-petroleum ether mixture (3:2). The main fractions were collected and concentrated to obtain a crude crystalline material, which was then admixed with 25 ml of ethyl acetate, and heated under shaking. This solution was gradually admixed with 200 ml of hexane, and a crystalline material thus formed was separated by filtration, washed in hexane and dried to give 1.018 g of compound D-1. Furthermore, the filtrate was concentrated, and refined by a silica gel column chromatography, wherein use was made, as eluant, of a petroleum ether-chloroform-ethyl acetate mixture (16:4:1), so that 0.183 g of compound D-1 was further obtained. The total amount of compound D-1 produced was 1.201 g (yield: 73%).

Compound D-1: light yellowish white powder.

¹H-NMR(200 MHz), CDCl₃, (ppm): 4.07 (s, 3H), 5.32 (s, 2H), 6.13 (s, 2H), 7.26 (s, 1H), 7.34–7.46 (m, 3H), 7.58 (dd, J=8.0 & 1.6 Hz, 2H), 7.61 (d, J=9.0 Hz, 1H), 7.84 (d, J=9.0 Hz, 1H), 8.34 (d, J=9.0 Hz, 1H), 8.36 (d, J=9.0 Hz, 1H), 8.69 (s, 1H), 9.75 (s, 1H).

¹³C-NMR(50 MHz), CDCl₃, (ppm): 50.03(q), 76.21(t), 101.62(t), 102.46(d), 104.68(d), 118.57(d), 118.69(d), 119.02(d), 120.27(s), 122.48(s), 127.40(d), 128.43(s), 128.67(d), 128.87(d)×2, 128.96(d)×2, 129.51(s), 130.11(s), 137.59(s), 140.37(s), 144.38(s), 147.22(d), 148.71(s), 148.89(s), 149.91(s).

IR(KBr), (cm⁻¹): 3032, 3004, 2964, 2944, 2910, 2875, 2840, 1640, 1616, 1595, 1578, 1533, 1495, 1460(vs), 1440 (s), 1394, 1378, 1358, 1324, 1284(s), 1277(s), 1251(s), 1223, 1202(s), 1169, 1136, 1112, 1081(s), 1040(s), 991, 968, 958, 949, 920, 904, 875, 850, 845, 830, 795, 759, 750, 697, 686, 667.

EXAMPLE 8-2

Synthesis of 2,3-(methylenedioxy)-7-benzyloxy-8-methoxybenzo[c]phenanthridine (compound D-1)

1.00 g (2.44 mmol) of compound C-1 and 1.87 g (4.07 mmol) of tri-n-octyltin hydride were dissolved in 100 ml of toluene, and the resulting solution was heated to 100° C. To this solution, 0.586 g of 2,2'-azobis(2-methyl butyronitrile) were added. After 70 minutes, the reaction solution was cooled to room temperature, then admixed with 1.2 g of active manganese dioxide, and stirred for 30 minutes. Next, the manganese compound was separated off by filtration, and the filtrate was concentrated under reduced pressure. To the residue 2.4 ml of chloroform was added, and heated under reflux for 10 minutes. The solution was coded to room temperature, then gradually admixed with 9.4 ml of hexane, and a crystalline material thus formed was separated by filtration, washed in hexane and dried to give 0.483 g (yield: 54.0%) of compound D-1.

EXAMPLE 9

Synthesis of 2,8-dimethoxy-3-isopropoxy-7-benzyloxybenzo[c]phenantridine (compound D-3)

886 mg of compound C-3 were subjected to a reaction operation in a manner similar to that of Example 8. 512 mg of compound D-3 was obtained (yield: 68%).

Compound D-3: light yellowish white powder.

¹H-NMR(200 MHz), CDCl₃, (ppm): 1.54 (d, J=6.1 Hz, 6h), 4.04 (s, 3H), 4.06 (s, 3H), 5.05 (septet, J=6.1 Hz, 1H), 5.31 (s, 2H), 7.28 (s, 1H), 7.34–7.47 (m, 3H), 7.55–7.61 (m, 2H), 7.59 (d, J=9.0 Hz, 1H), 7.86 (d, J=9.0 Hz, 1H), 8.33 (d, J=9.0 Hz, 1H), 8.35 (d, J=9.0 Hz, 1H), 8.77 (s, 1H), 9.77 (s, 1H)

IR(KBr), (cm⁻¹): 2976, 2938, 2838, 1618, 1576, 1525, 1509, 1479, 1461, 1434, 1411, 1389, 1372, 1351, 1324, 1282, 1265(s), 1218, 1203, 1168, 1143, 1115, 1080, 1068, 1026, 981, 953, 929, 915, 880, 856, 842, 830, 797, 759, 747, 698, 685

EXAMPLE 10

Synthesis of 2-isopropoxy-3,8-dimethoxy-7-benzyloxybenzo[c]phenantridine (compound D-4)

720 mg of compound C-4 were subjected to a reaction operation in a manner similar to that of Example 8. 320 mg of compound D-4 was obtained (yield: 53%).

Compound D-4: light yellowish white powder.

¹H-NMR(200 MHz), CDCl₃, (ppm): 1.51 (d, J=6.0 Hz, 6H), 4.07 (s, 3H), 4.17 (s, 3H), 4.80 (septet, J=6.0 Hz, 1H), 5.32 (s, 2H), 7.32 (s, 1H), 7.34–7.47 (m, 3H), 7.55–7.62 (m, 2H), 7.62 (d, J=9.0 Hz, 1H), 7.86 (d, J=9.0 Hz, 1H), 8.36 (d, J=9.0 Hz, 1H), 8.39 (d, J=9.0 Hz, 1H), 8.72 (s, 1H), 9.79 (s, 1H).

IR(KBr), (cm$^{-1}$): 2976, 2938, 2840, 1618, 1578, 1527, 1509, 1478, 1456, 1435, 1409, 1389, 1375, 1355, 1325, 1267(s), 1220, 1191, 1177, 1163, 1140, 1112, 1083, 1067, 1021, 995, 973, 942, 911, 872, 849, 830, 804, 772, 759, 749, 698.

EXAMPLE 11

Synthesis of 2,3-diisopropoxy-7-benzyloxy-8-methoxybenzo[c]phenantridine (compound D-6)

692 mg of compound C-6 were subjected to a reaction operation in a manner similar to that of Example 8. 379 mg of compound D-6 was obtained (yield: 64%).

Compound D-6: light yellowish white powder.

$^1$H-NMR(200 MHz), CDCl$_3$, (ppm): 1.45 (d, J=6.1 Hz, 6H), 1.49 (d, J=6.1 Hz, 6H), 4.04 (s, 3H), 4.69 (septet, J=6.1 Hz, 1H), 4.92 (septet, J=6.0 Hz, 1H), 5.31 (s, 2H), 7.34–7.46 (m, 3H), 7.36 (s, 1H), 7.55–7.62 (m, 2H), 7.58 (d, J=9.0 Hz, 1H), 7.83 (d, J=9.0 Hz, 1H), 8.31 (d, J=9.0 Hz, 1H), 8.34 (d, J=9.0 Hz, 1H), 8.78 (s, 1H), 9.77 (s, 1H).

IR(KBr), (cm$^{-1}$): 2976, 2932, 1617, 1576, 1527, 1507, 1463, 1439, 1413, 1385, 1373, 1355, 1323, 1265(s), 1216, 1180, 1166, 1139, 1113, 1086, 1066, 998, 952, 932, 910, 876, 856, 831, 800, 743, 697.

EXAMPLE 12

Synthesis of 7-benzyloxy-8-methoxy-benzo[c]phenantridine (compound D-7)

3.71 g of compound C-7 were subjected to a reaction operation in a manner similar to that of Example 8. 1.387 g of compound D-7 was obtained (yield: 46%). Compound D-7: light yellowish white powder.

$^1$H-NMR(200 MHz), CDCl$_3$, (ppm): 4.08 (s, 3H), 5.34 (s, 2H), 7.34–7.47 (m, 3H), 7.55–7.61 (m, 2H), 7.64 (d, J=9.0 Hz, 1H), 7.61–7.71 (m, 1H), 7.71–7.81 (m, 1H), 7.97 (dd', J=8.0 & 1.3 Hz, 1H), 8.00 (d, J=9.0 Hz, 1H), 8.41 (d, J=9.0 Hz, 1H), 8.48 (d, J=9.0 Hz, 1H), 9.36 (dd, J=8.0 & 1.0 Hz, 1H), 9.84 (s, 1H).

IR(KBr), (cm$^{-1}$): 3025, 2985, 2925, 2870, 2830, 1617, 1574, 1525, 1464, 1442, 1425, 1355, 1332, 1291(s), 1281(s), 1261, 1236, 1204, 1177, 1154, 1138, 1079(s), 1024, 986, 958, 934, 901, 868, 843, 834, 809(s), 816, 744, 721, 695.

The following Examples relate to the production of compounds having the general formula A. These compounds may also be present in another form represented by the general formula E. So, the physical properties of the latter isomers are also given in the Examples, as far as such data were obtained.

EXAMPLE 13

Synthesis of 2,3-(methylenedioxy)-5-methyl-7-hydroxy-8-methoxy-benzo[c]phenanthridinium hydrogen sulfate (compound A-0)

1.00 g (2.44 mmol) of compound D-1, 4.55 g (24.4 mmol) of methyl p-toluenesulfonate and 2.91 g (24.5 mmol) of KBr were sufficiently mixed with one another with the aid of a magnetic stirrer. The resulting mixture was then heated to 130° C. for 5.5 hours, diluted with water, extracted with methylene chloride, dried over anhydrous sodium sulfate, filtered, and concentrated. The concentrated residual material thus obtained was again admixed with 4.55 g of methyl p-toluenesulfonate and 2.91 g of powdery KBr with the aid of a magnetic stirrer, and then heated to 130° C. for 3 hours.

Next, the reaction mixture was admixed with 5 ml of acetic acid and 2.5 ml of concentrated hydrochloric acid, and heated to 100° C. for 2 hours. After that, the reaction mixture was diluted with water, and neutralized by portionwise adding sodium hydrogen carbonate. The reaction mixture was extracted with methylene chloride, dried over anhydrous sodium sulfate, filtered and concentrated. Then the reaction mixture was subjected to a silica gel column chromatography, wherein use was made, as eluant, of a methylene chloride-methanol mixture (9:1). The fractions, which contained a pure compound E-0, were collected and concentrated.

The concentrated product, containing compound E-0, was gradually added to a dilute aqueous sulfuric acid solution containing 5 ml of a 0.5M aqueous sulfuric acid solution, 25 ml of water and ice. The resulting mixture was concentrated, and then admixed with 5 ml of fresh water to dissolve a large portion of compound A-0 in the water. Thereafter, the aqueous solution thus obtained was gradually admixed with 200 ml of acetone to form a yellow precipitate, which was then separated by filtration, and dried in vacuum, whereby 750 mg of compound A-0 was obtained (yield: 71.2%).

Compound E-0: dark violet solid material $^1$H-NMR(200 MHz), DMSO-d$_6$, (ppm): 3.76 (s, 3H), 4.41 (s, 3H), 6.25 (s, 2H), 7.04 (d, J=8.0 Hz, 1H), 7.20 (d, J=8.0 Hz, 1H), 7.55 (s, 1H), 7.90 (d, J=9.0 Hz, 1H), 7.98 (s, 1H), 8.27 (d, J=9.0 Hz, 1H), 9.02 (s, 1H).

$^{13}$C-NMR(50 MHz), DMSO-d$_6$, (ppm): 48.65(q), 55.59 (q), 100.04(d), 102.29(t), 103.22(d), 105.52(d), 118.54(s), 119.13(d), 119.36(s), 120.64(s), 125.41(s), 127.04(d), 128.30(d), 131.48(s), 131.63(s), 147.90(s), 148.09(s), 151.06(d), 151.21(s), 168.30(s)

IR(KBr), (cm$^{-1}$): 3050, 2964, 2910, 2834, 1625(s), 1584, 1559, 1538(s), 1511(s), 1501(s), 1474(s), 1459, 1417, 1372 (s), 1336, 1287, 1256(vs), 1245(vs), 1207, 1180, 1145, 1122, 1114, 1098, 1042(s), 968, 940, 922, 891, 872, 864, 855, 828, 804, 790, 764, 745, 710, 680, 660.

Compound A-0: yellow powder (X$^-$=HSO$_4^{-1}$)

$^1$H-NMR(200 MHz), D$_2$O, (ppm): 3.62 (s, 3H), 3.94 (br s, 3H), 5.95 (br s, 2H), 6.39 (s, 1H), 6.78 (s, 1H), 6.86 (d, J=9.0 Hz, 1H), 6.94 (d, J=9.0 Hz, 1H), 7.02 (d, J=9.0 Hz, 1H), 7.06 (d, J=9.0 Hz, 1H), 8.56 (s, 1H)

$^{13}$C-NMR(50 MHz), D$_2$O, (ppm): 54.93(q), 58.96(q), 105.51(d), 106.16(t), 108.33(d), 115.55(d) & (s), 119.54(d), 121.05(s), 125.69(s), 125.81(d), 127.67(s), 131.13(s), 133.47(d), 133.90(s), 146.94(s), 147.97(s), 150.79(s), 151.54(d) & (s)

IR(KBr), (cm$^{-1}$): 3476, 3040, 3010, 2950, 1628, 1603, 1585, 1549, 1493(s), 1478(s), 1466, 1447, 1415, 1373, 1353, 1338, 1297(s), 1279(s), 1260(s), 1218(s), 1191(s), 1156, 1112, 1096, 1053, 1038(s), 967, 919, 865, 847, 830, 778, 764, 751, 709.

EXAMPLE 14

Synthesis of 2,3-(methylenedioxy)-5-ethyl-7-hydroxy-8-methoxy-benzo[c]phenanthridinium hydrogen sulfate (compound A-1)

1.433 g (3.5 mmol) of 2,3-(methylenedioxy)-7-benzyloxy-8-methoxy-benzo[c]phenanthridine (compound D-1) was admixed with 0.906 ml (3.7 mmol) of ethyl trifluoromethanesulfonate and 10 ml of dry toluene, and heated to 100° C. for 4.5 hours. Thereafter, the resultant mixture was admixed with 10 ml of acetic acid and 5 ml of concentrated hydrochloric acid, and heated to 100° C. for 1 hour. After that, the reaction mixture was diluted by gradually adding the reaction mixture to ice water. The reaction mixture was then neutralized by portionwise adding sodium hydrogen carbonate. Thereafter, an extraction operation was effected with chloroform. The chloroform extract layer was dried over anhydrous sodium sulfate, filtered, and concentrated under reduced pressure. The residue thus obtained was refined by a silica gel chromatography, wherein use was made, as eluant, of a chloroform-methanol mixture (9:1). The main fractions were collected and concentrated to obtain a dark violet solid material, which was compound E-1 having a structure represented by the general formula E. Then, compound E-1 was dissolved in a small amount of methanol, and the resulting solution was acidified by gradually adding thereto a dilute aqueous sulfuric acid solution in an amount of from 1.0 to 2.0 mol per 1 mol of compound E-1. By this treatment, the color of the solution was changed into yellow or orange. Thereafter, the solution was concentrated under reduced pressure, and the concentrated aqueous solution was portionwise added with acetone under shaking to form a precipitate, which was separated by filtration and dried, so that compound A-1, wherein $X^-=HSO_4^-$, was obtained as yellow powder in an amount of 1.171 g (yield: 75.1%).

Compound E-1: dark violet solid material.

$^1$H-NMR(200 MHz), CDCl$_3$+CD$_3$OD (1:1), (ppm): 1.65 (t, J=7.2 Hz, 3H), 3.95 (s, 3H), 4.83 (q, J=7.2 Hz, 2H), 6.19 (s, 2H), 7.30 (s, 1H), 7.30 (d, J=8.2 Hz, 1H), 7.44 (d, J=8.2 Hz, 1H), 7.56 (s, 1H), 7.81 (d, J=8.9 Hz, 1H), 8.18 (d, J=8.9 Hz, 1H), 9.36 (s, 1H)

$^{13}$C-NMR(50 MHz), CDCl$_3$+CD$_3$OD (1:1), (ppm): 16.65 (q), 54.90(t), 56.36(q), 102.71(d), 103.14(t), 103.54(d), 106.56(d), 119.61(d), 119.77(s), 120.94(d), 121.47(s), 127.20(s), 128.10(s), 129.37(d), 131.33(s), 132.58(s), 149.29(s), 149.71(s), 150.84(d), 152.12(s), 168.45(s).

IR(KBr), (cm$^{-1}$): 2970, 2918, 1623(s), 1582, 1558, 1534 (s), 1502(s), 1475(s), 1460(s), 1376(s), 1345, 1300, 1285, 1250(vs), 1189, 1142, 1115, 1099, 1036(s), 941, 864, 794, 761, 736, 707, 673, 664.

Compound A-1: yellow powder ($X^-=HSO_4^-$)

$^1$H-NMR(200 MHz), D$_2$O, (ppm): 1.64 (br t, J=6.3 Hz, 3H), 3.63 (s, 3H), 4.27 (br m, 2H), 6.02 (br s, 2H), 6.45 (s, 1H), 6.55 (br s, 1H), 6.81 (d, J=9.0 Hz, 1H), 6.95 (br, s, 2H), 7.05 (d, J=9.0 Hz, 1H), 8.79 (s, 1H).

$^{13}$C-NMR(50 MHz), D$_2$O, (ppm): 19.32(q), 58.78(q), 59.43(t), 104.40(d), 105.92(t), 108.03(d), 115.24(d), 115.63 (s), 119.17(d), 120.05(s), 125.49(s) & (d), 127.39(s), 130.66 (s), 132.96(d), 133.33(s), 146.54(s), 147.55(s), 150.25(d), 150.59(s), 151.46(s).

IR(KBr), (cm$^{-1}$): 3364, 3040, 2970, 2930, 2888, 1622, 1602, 1550, 1491(s), 1474(s), 1453, 1412, 1383, 1348, 1334, 1300, 1279(s), 1260(s), 1223(s), 1217(s), 1158, 1128, 1115, 1103, 1080, 1042(s), 942, 925, 884, 825, 771.

EXAMPLE 15

Synthesis of 2,3-(methylenedioxy)-5-(n-propyl)-7-hydroxy-8-methoxy-benzo[c]phenanthridinium hydrogen sulfate (compound A-2)

Compound D-1 and n-propyl 2-nitrobenzenesulfonate sulfonate were subjected to a reaction operation in a manner similar to that of Example 14 to produce compound E-2, which was then treated with dilute sulfuric acid in the presence of methanol, whereby compound A-2, wherein $X^-=HSO_4^-$, was obtained.

Compound A-2: yellow powder ($X^-=HSO_4^-$)

$^1$H-NMR(200 MHz), D$_2$O, (ppm): 0.97 (br t, J=7.1 Hz, 3H), 1.95 (br m, 2H), 3.79 (s, 3H), 4.22 (br m, 2H), 6.12 (br s, 2H), 6.55 (br s, 1H), 6.65 (s, 1H), 7.10 (d, J=9.0 Hz, 1H), 7.16 (d, J=9.0 Hz, 1H), 7.26 (d, J=9.0 Hz, 1H), 7.30 (d, J=9.0 Hz, 1H), 8.97 (S, 1H)

$^{13}$C-NMR(50 MHz) D$_2$O, (ppm) 12.40(q), 27.92(t), 59.22 (q), 65.30(t), 104.49(d), 106.31(t), 108.62(d), 116.05(d), 116.30(s), 120.09(d), 120.79(s), 126.27(d), 126.40(s), 128.26(s), 131.31(s), 133.53(d), 134.08(s), 147.41(s), 148.36(s), 151.10(d), 151.27(s), 152.02(s)

IR(KBr), (cm$^{-1}$): 3394, 3064, 2982, 1647, 1620, 1602, 1581, 1550, 1493(s), 1472(s), 1417, 1387, 1375, 1355, 1302(s), 1277(s), 1257(s), 1215(s), 1172(s), 1155, 1139, 1117, 1105, 1082, 1062, 1039(s), 1001, 971, 934, 926, 886, 855(s), 829, 811, 790, 759, 707

EXAMPLE 16

Synthesis of 2,8-dimethoxy-3,7-dihydroxy-5-methylbenzo[c]phenanthridinium chloride (compound A-3)

227 mg (0.5 mmol) of 2,8-dimethoxy-3-isopropoxy-7-benzyloxy-benzo[c]phenanthridine (compound D-3) was admixed with 932 mg (5 mmol) of methyl p-toluenesulfonate and 35 mg (0.25 mmol) of anhydrous potassium carbonate, and the resultant mixture was heated to 140° C. for 3.5 hours. Then the mixture was admixed with 6 ml of acetic acid and 3 ml of concentrated hydrochloric acid, and heated to 100° C. for 3 hours. After that, the reaction mixture was gradually added to ice water to obtain a dilute mixture, which was then neutralized by portionwise adding thereto sodium hydrogen carbonate. The neutralized mixture was extracted with chloroform and a small amount of methanol. The extract was dried over anhydrous sodium sulfate, filtered, and concentrated under reduced pressure. The residue thus obtained was refined by a silica gel chromatography, wherein use was made, as eluant, of a chloroform-methanol mixture (4:1). The main fractions were collected and concentrated to give a dark violet solid material, which was compound E-3 having a structure represented by the general formula E. Then, compound E-3 was dissolved in a small amount of methanol, and acidified by gradually adding thereto a dilute aqueous solution of hydrochloric acid in an amount of from 1.5 to 3.0 mol per 1 mol of the compound, so that the color of the solution of the compound was changed into yellow or orange. The solution was concentrated under reduced pressure to remove the solvent and the excess hydrochloric acid. The residue thus obtained was compound A-3, wherein $X^-=Cl^-$. The amount of compound A-3 produced was 98 mg (yield: 52.7%).

Compound A-3: yellow powder ($X^-=Cl^-$).

$^1$H-NMR(200 MHz), OD$_3$OD(+DCl), (ppm): 4.09 (s, 3H), 4.11 (s, 3H), 4.95 (s, 3H), 7.62 (s, 1H), 8.08 (d, J=9.0 Hz, 1H), 8.16 (s, 1H), 8.20 (d, J=9.0 Hz, 1H), 8.39 (d, J=9.0 Hz, 1H), 8.55 (d, J=9.0 Hz, 1H), 9.94 (s, 1H).

IR(KBr), (cm$^{-1}$): 3428, 3082, 1621, 1591, 1578, 1554, 1504, 1448, 1415, 1384, 1374, 1352, 1339, 1289(s), 1276(s), 1220, 1193, 1167, 1157, 1114, 1061, 1025, 1008, 966, 921, 865, 854, 818, 781, 748.

EXAMPLE 17

Synthesis of 2,7-dihydroxy-3,8-dimethoxy-5-methylbenzo[c]phenanthridinium chloride (compound A-4)

2-isopropoxy-3,8-dimethoxy-7-benzyloxybenzo[c] phenanthridine (compound D-4) and methyl p-toluenesulfonate were subjected to a reaction operation in a manner similar to that of Example 16 to produce compound E-4, which was further treated with dilute hydrochloric acid in the presence of methanol, so that compound A-4, wherein $X^-=Cl^-$, was obtained.

Compound A-4: yellow powder ($X^-=Cl^-$).

$^1$H-NMR(200 MHz), OD$_3$OD(+DCl), (ppm): 4.11 (s, 3H), 4.17 (s, 3H), 5.03 (s, 3H), 7.49 (s, 1H), 8.08 (d, J=9.1 Hz, 1H), 8.09 (s, 1H), 8.12 (d, J=9.1 Hz, 1H), 8.39 (d, J=9.1 Hz, 1H), 8.57 (d, J=9.1 Hz, 1H), 9.98 (s, 1H).

$^{13}$C-NMR(50 MHz), CD$_3$OD(+DCl), (ppm): 52.74(q), 57.05(q), 57.75(q), 108.55(d), 113.59(d), 115.20(d), 117.09 (s), 119.49(d), 120.14(s), 125.88(d), 126.98(s), 129.99(s), 132.13(d), 133.20(s), 133.46(s), 147.62(s), 150.80(s), 151.11(s)×2, 151.63(d).

IR(KBr), (cm$^{-1}$): 3384, 3214, 1619, 1589, 1576, 1556, 1504, 1457, 1445, 1421, 1414, 1378, 1350, 1338, 1301(s), 1279(s), 1262(s), 1217, 1168, 1155, 1115, 1058, 1022, 1006, 976, 935, 866, 828, 818, 808, 785, 747, 723.

EXAMPLE 18

Synthesis of 2,3,7-trihydroxy-5-methyl-8-methoxybenzo[c]phenanthridinium tosylate (compound A-6)

2,3-diisopropoxy-7-benzyloxy-8-methoxybenzo[c] phenanthridine (compound D-6) and methyl p-toluenesulfonate were subjected to a reaction operation in a manner similar to Example 16 to produce compound E-6, which was further treated with p-toluenesulfonic acid in the presence of methanol, so that compound A-6, wherein $X^-=OTs^-$, was obtained.

Compound A-6: yellow powder ($X^-=OTs^-$).

$^1$H-NMR(200 MHz), CD$_3$OD+D$_2$O(+DCl), (ppm) 4.00 (s, 3H), 4.67 (s, 3H), 7.17 (s, 1H), 7.73–7.80 (m, 3H), 7.92 (br d, J=9.0 Hz, 1H), 8.35 (br d, J=9.0 Hz, 1H), 9.44 (s, 1H); OTs$^-$ moiety (Ts=p-Toluenesulfonyl): 2.38 (s, 3H), 7.31 (br d, J=8.0 Hz, 2H), 7.67 (br d, J=8.0 Hz, 2H).

IR(KBr), (cm$^{31}$ $^1$): 3390, 3200–3050, 1622, 1562, 1495, 1459, 1454, 1445, 1407, 1384, 1352, 1339, 1295(s), 1274(s), 1217, 1189, 1148, 1118(s), 1056, 1033, 1009, 978, 927, 871, 815, 784, 744, 717, 681, 671.

EXAMPLE 19

Synthesis of 5-ethyl-7-hydroxy-8-methoxy-benzo[c] phenanthridinium hydrogen sulfate (compound A-7)

183 mg (0.5 mmol) of 7-benzyloxy-8-methoxybenzo[c] phenanthridine (compound D-7) were admixed with 0.13 ml (1.0 mmol) of ethyl trifluoromethanesulfonate and 0.9 ml of dry toluene, and the resulting mixture was heated to 100° C. for 5 hours. After that, the mixture was admixed with 4 ml of acetic acid and 1 ml of concentrated hydrochloric acid, and heated to 100° C. for 1 hour. Thereafter, the reaction mixture was gradually added to ice water. The reaction mixture thus diluted was neutralized by portionwise adding thereto sodium hydrogen carbonate, and then extracted with chloroform. The chloroform extract layer was dried over anhydrous sodium sulfate, filtered, and concentrated under reduced pressure. The resultant residue was refined by a silica gel chromatography, wherein use was made, as eluant, of a chloroform-methanol mixture (9:1). The main fractions were collected and concentrated to obtain a dark violet solid material, which was compound E-7 having a structure represented by the general formula E. Next, compound E-7 was dissolved in a small amount of methanol, and the solution thus obtained was acidified by portionwise adding thereto a dilute aqueous solution of sulfuric acid in an amount of from 1.0 to 2.0 mol per 1 mol of the compound, so that the color of the solution of the compound was changed into yellow or orange. The aqueous solution of the compound was then concentrated under reduced pressure. Acetone was added portionwise to the concentrated solution under shaking to form a precipitate, which was separated by filtration, and dried, so that the aimed compound A-7, wherein $X^-=HSO_4^-$, was obtained as yellow powder in an amount of 160 mg (yield: 79.7%).

Compound E-7: dark violet solid material.

$^1$H-NMR(200 MHz), DMSO-d$_6$, (ppm): 1.45 (t, J=7.1 Hz, 3H), 3.78 (s, 3H), 4.82 (q, J=7.1 Hz, 2H), 7.10 (d, J=8.0 Hz, 1H), 7.21 (d, J=8.0 Hz, 1H), 7.63–7.76 (m, 2H), 8.03 (d, J=8.8 Hz, 1H), 8.08–8.14 (m, 1H), 8.32–8.41 (m, 1H), 8.40 (d, J=8.8 Hz, 1H), 9.11 (s, 1H).

$^{13}$C-NMR(50 MHz), DMSO-d$_6$, (ppm): 15.96(q), 53.13 (t), 55.23(q), 99.29(d), 117.77(d), 118.88(s), 120.57(d), 123.89(s), 124.56(d), 126.38(s), 126.54(s), 126.61(d), 126.68(f), 128.08(d), 128.86(d), 130.38(s), 133.47(s), 148.66(d), 151.53(s), 169.42(s).

IR(KBr), (cm$^{-1}$): 3039, 2986, 2938, 2832, 1628(s), 1614 (s), 1557(s), 1530(s), 1510(s), 1495, 1474, 1456, 1423, 1386, 1377(s), 1354, 1345, 1335, 1317, 1287, 1266(s), 1245(s), 1239(s), 1194, 1155, 1139, 1101(s), 1075, 1061, 1046, 977, 945, 923, 907, 871, 823, 798, 792, 774(s), 752, 691, 675.

Compound A-7: yellow powder ($X^-=HSO_4^-$)

$^1$H-NMR(200 MHz), D$_2$O, (ppm): 1.72 (t, J=7.0 Hz, 3H), 3.56 (s, 3H), 4.52 (br q, J=7.0 Hz, 2H), 6.95 & 7.05 (AB, JAB=9.2 Hz, each 1H), 7.21 (br s, 2H), 7.32–7.50 (m, 2H), 7.38 (br d, J=7.9 Hz, 1H), 7.59 (br d, J=7.9 Hz, 1H), 8.96 (s, 1H)

$^{13}$C-NMR(50 MHz), D$_2$O, (ppm): 19.21(q), 58.82(q), 59.83(t), 115.65(d), 116.24(s), 120.59(d), 124.28(s), 125.66 (d), 127.01(s) & (d), 127.52(s), 131.05(d), 131.38(s) & (d), 132.25(d), 134.28(d), 135.72(s), 146.64(s), 147.90(s), 150.21(d)

IR(KBr), (cm$^{-1}$): 3419, 3052, 1614, 1583, 1540, 1497, 1468, 1446, 1431, 1384, 1361, 1341, 1302(s), 1277(s), 1216(s), 1164, 1150, 1143, 1130, 1086, 1059, 985, 921, 854, 821, 767, 695

EXAMPLE 20

Synthesis of 5-methyl-7-hydroxy-8-methoxy-benzo [c]phenanthridinium hydrogen sulfate (compound A-8)

The starting material used here was compound E-8 prepared according to a method described in J. Org. Chem., 53, 1708–1713 (1988). Compound E-8 was subjected to a reaction operation to form compound A-8, in a manner similar to that of Example 14 directed to the conversion of compound E-1 into the corresponding hydrogen sulfate salt. Compound A-8 was obtained in a yield of 99.0%.

Compound A-8: yellow powder ($X^-=HSO_4^-$).

$^1$H-NMR(200 MHz), D$_2$O, (ppm): 3.42 (s, 3H), 4.08 (s, 3H), 6.79 & 6.85 (AB, JAB=9.1 Hz, each 1H), 7.03 (br s, 2H), 7.16–7.24 (m, 1H), 7.24–7.34 (m, 2H), 7.63–7.73 (m, 1H), 8.61 (s, 1H).

$^{13}$C-NMR(50 MHz), D$_2$O, (ppm): 54.98(q), 58.81(q), 115.64(d), 115.87(s), 120.58(d), 124.93(s), 125.69(d), 126.84(s), 127.36(s), 127.98(d), 131.01(d), 131.60(d) & (s), 132.41(d), 134.66(s), 136.01(s), 146.82(s), 148.09(s), 151.29(d).

IR(KBr), (cm$^{-1}$): 3480, 3000, 2950, 1624, 1617, 1583, 1537, 1488, 1463, 1450, 1430, 1381, 1359, 1339, 1318, 1295(s), 1278(s), 1263, 1241, 1228(s), 1196, 1182, 1167, 1143, 1112(s), 1085, 1066, 982, 922, 914, 875, 853, 823(s), 783, 766, 751, 702, 692, 670.

EXAMPLE 21

Pharmaceutical composition 1 g of 2,3-(methylenedioxy)-5-methyl-7-hydroxy-8-methoxy-benzo[c]phenanthridinium hydrogen sulfate (compound A-0), wherein X$^-$=HSO$_4^-$, 1 g of polysolvate and 1 g of Macrogol 400 were dissolved in 100 g of distilled water for injection, to form a solution. After filtering through a membrane filter, the solution was separately charged in ampules, and lyophilized in a conventional manner to give a preparation for injection containing 50 mg of compound A-0 per ampule.

EXAMPLE 22

Pharmaceutical composition 1 g of 2,3-(methylenedioxy)-5-ethyl-7-hydroxy-8-methoxy-benzo[c]phenanthridinium hydrogen sulfate (compound A-1), wherein X$^-$=HSO$_4^-$, 1 g of polysolvate and 1 g of Macrogol 400 were dissolved in 100 g of distilled water for injection, to form a solution. After filtering through a membrane filter, the solution was separately charged in ampoules, and lyophilized in a conventional manner to give a preparation for injection containing 50 mg of compound A-1 per ampoule.

We claim:

1. A pharmaceutical composition comprising as an effective ingredient a benzo[c]phenanthridinium derivative of the general formula A:

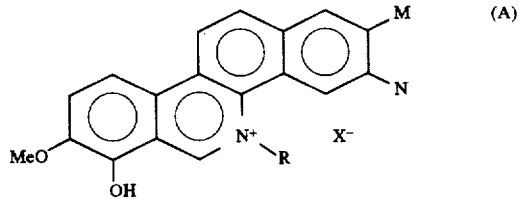

wherein M and N together form a methylenedioxy group, X$^-$ represents a hydrogen acid residue, and R represents a lower alkyl group and pharmaceutically acceptable additives.

2. A pharmaceutical composition according to claim 1, wherein the said hydrogen acid residue is a hydrogen sulfate ion HSO$_4^-$.

3. A pharmaceutical composition according to claim 1, wherein R represents a methyl group.

4. A method for inhibiting growth and metastasis and for the treatment of tumor in warm-blooded animal with tumor, which comprises administering to said warm-blooded animal an effective dose of a benzo[c]phenanthridinium derivative of the general formula A:

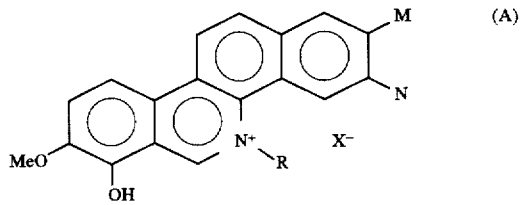

wherein M and N together form a methylenedioxy group, X$^-$ represents a hydrogen acid residue, and R represents a lower alkyl group.

5. A method according to claim 4, wherein the said hydrogen acid residue is a hydrogen sulfate ion HSO$_4^-$.

6. A method according to claim 4, wherein R represents a methyl group.

7. A benzo[c]phenanthridinium derivative of the general formula A:

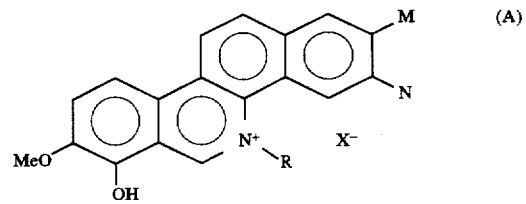

wherein M and N together form a methylenedioxy group, X$^-$ represents a hydrogen acid residue, and R represents a lower alkyl group.

8. A benzo[c]phenanthridinium derivative according to claim 7, wherein the hydrogen acid residue X$^-$ is a hydrogen sulfate ion HSO$_4^-$.

9. A 2,3-(methylenedioxy)-5-ethyl-7-hydroxy-8-methoxy-benzo[c]phenanthridinium hydrogen salt.

10. A 2,3-(methylenedioxy)-5-(n-propyl)-7-hydroxy-8-methoxy-benzo[c]phenanthridinium hydrogen salt.

11. A 2,3-(methylenedioxy)-5-methyl-7-hydroxy-8-methoxy-benzo[c]phenanthridinium hydrogen salt.

12. A 2,3-(methylenedioxy)-5-methyl-7-hydroxy-8-methoxy-benzo[c]phenanthridinium hydrogen sulfate.

* * * * *